(12) United States Patent
Corveleyn et al.

(10) Patent No.: US 10,596,207 B2
(45) Date of Patent: *Mar. 24, 2020

(54) CRYOPROTECTANTS FOR FREEZE DRYING OF LACTIC ACID BACTERIA

(71) Applicant: INTREXON ACTOBIOTICS NV, Zwijnaarde (BE)

(72) Inventors: Sam Corveleyn, Zwijnaarde (BE); Patrick Dhaese, Zwijnaarde (BE); Sabine Neirynck, Zwijnaarde (BE); Lothar Steidler, Zwijnaarde (BE)

(73) Assignee: INTREXON ACTOBIOTICS NV, Zwijnaarde (BE)

( * ) Notice: Subject to any disclaimer, the term of this patent is extended or adjusted under 35 U.S.C. 154(b) by 151 days.

This patent is subject to a terminal disclaimer.

(21) Appl. No.: 15/398,945

(22) Filed: Jan. 5, 2017

(65) Prior Publication Data

US 2017/0151292 A1 Jun. 1, 2017
US 2019/0160119 A9 May 30, 2019

Related U.S. Application Data

(63) Continuation of application No. 13/264,395, filed as application No. PCT/EP2010/002604 on Apr. 28, 2010, now Pat. No. 9,574,169.

(30) Foreign Application Priority Data

Apr. 30, 2009 (EP) .................................. 9100265

(51) Int. Cl.
*A61K 35/744* (2015.01)
*C12N 1/04* (2006.01)
(Continued)

(52) U.S. Cl.
CPC ............ *A61K 35/744* (2013.01); *A23K 20/10* (2016.05); *A23L 33/10* (2016.08); *A23L 33/135* (2016.08);
(Continued)

(58) Field of Classification Search
None
See application file for complete search history.

(56) References Cited

U.S. PATENT DOCUMENTS 3,897,307 A 7/1975 Porubcan et al.
5,559,007 A 9/1996 Suri et al.
(Continued)

FOREIGN PATENT DOCUMENTS

EP 0259739 A1 3/1988
EP 1441027 A1 7/2004
(Continued)

OTHER PUBLICATIONS

"Vegitone MRS broth" is webpages at https://www.sigmaaldrich.com/catalog/search?interface=All&term=MRS+Broth&N=0+9671942&mode=partialmax&focus=product&lang=en&region=US, https://www.sigmaaldrich.com/catalog/product/sial/38944?lang=en&region=US, online since Feb. 1, 2002 according to Google (Year: 2002).*
(Continued)

*Primary Examiner* — Renee Claytor
*Assistant Examiner* — Trent R Clarke
(74) *Attorney, Agent, or Firm* — Drinker Biddle & Reath LLP

(57) ABSTRACT

The present invention comprises the discovery and development of an effective cryoprotectant composition, without containing skim milk or any other animal-derived compounds, to achieve long-term stability of freeze-dried lactic acid bacteria (LAB), at different temperatures, whereby the retention of viability of the freeze-dried LAB after 6 months
(Continued)

of storage, preferably after 9 months of storage, more preferably after 12 months of storage is more than 50%. The invention is in the field of producing freeze dried bacteria, in particular Lactic acid bacteria. More in particular, the invention relates to the use of a novel combination of cryoprotectants for increasing the viability of bacteria after freeze drying, improving the texture of the lyofilized cake for easy grinding and improving the long term stability of the freeze dried bacteria at different temperature conditions. The invention further relates to such freeze dried bacteria for use in food industry or in human or animal health applications. More in particular, the invention relates to the increased viability and long-term storage of recombinant bacteria capable of expressing heterologous proteins or peptides and administered to humans or animals for therapeutic or vaccination purposes.

19 Claims, 4 Drawing Sheets

Specification includes a Sequence Listing.

(51) Int. Cl.
| | |
|---|---|
| A23K 20/10 | (2016.01) |
| A23L 33/10 | (2016.01) |
| A23L 33/135 | (2016.01) |
| A61K 47/10 | (2017.01) |
| A61K 47/12 | (2006.01) |
| A61K 47/36 | (2006.01) |
| C12N 1/20 | (2006.01) |

(52) U.S. Cl.
CPC .............. *A61K 47/10* (2013.01); *A61K 47/12* (2013.01); *A61K 47/36* (2013.01); *C12N 1/04* (2013.01); *C12N 1/20* (2013.01); *A23V 2002/00* (2013.01); *A23Y 2240/41* (2013.01)

(56) References Cited

U.S. PATENT DOCUMENTS

| 7,435,422 | B2 | 10/2008 | Warthen et al. |
|---|---|---|---|
| 2005/0075298 | A1 | 4/2005 | Chen et al. |
| 2005/0100559 | A1 | 5/2005 | Myatt et al. |
| 2009/0041727 | A1 | 2/2009 | Suzuki et al. |

FOREIGN PATENT DOCUMENTS

| JP | 2008/516591 A | 5/2008 |
|---|---|---|
| WO | WO-1995/010601 A1 | 4/1995 |
| WO | WO-96/11277 A1 | 4/1996 |
| WO | WO-97/14806 A2 | 4/1997 |
| WO | WO-00/23471 A2 | 4/2000 |
| WO | WO-01/02570 A1 | 1/2001 |
| WO | WO-04/065584 A1 | 8/2004 |
| WO | WO-2006/040257 A1 | 4/2006 |

OTHER PUBLICATIONS

Bibiloni et al., "VSL#3 Probiotic-Mixture Induces Remission in Patients with Active Ulcerative Colitis" American Journal of Gastroenterology, vol. 100, No. 7, pp. 1539-1546, 2005.
Rioux et al., "Probiotics in the Treatment of Inflammatory Bowel Disease," Journal of Clinical Gastroenterology, vol. 40, No. 3, pp. 260-263, 2006.
Shanahan, Fergus, "Probiotics in inflammatory bowel disease—therapeutic rationale and role" Advanced Drug Delivery Reviews, vol. 56, No. 6, pp. 809-818, 2004.
Carvalho et al., Relevant factors for the preparation of freeze-dried lactic acid bacteria International Dairy Journal, col. 14, No. 10, pp. 835-847, 2004.
Miyamoto-Shinohara et al., "Survival of freeze-dried bacteria," Journal of Applied Microbiology, vol. 54, No. 1, pp. 9-24, 2008.
Braat et al., "A Phase I Trial with Transgenic Bacteria Expressing Interleukin-10 in Crohn's Disease," Clinical Gastroenterology and Hepatology, vol. 4, pp. 754-759, 2006.
Vandenbroucke et al., "Active Delivery of Trefoil Factors by Genetically Modified Lactococcus lactis Prevents and Heals Acute Colitis in Mice," Gastroenterology, vol. 127, pp. 502-513, 2004.
Steidler et al. "Biological Containment of Genetically Modified Lactococcus lactis for Intestinal Delivery of Human Interleukin 10," Nature Biotechnology, vol. 21, pp. 785-789, 2003.
Steidler et al., "Secretion of Biologically Active Murine Interleukin-2 by *Lactococcus lactis* subsp. lactis," Applied and Environmental Microbiology, vol. 61, pp. 1627-1629, 1995.
Steidler et al., Mucosal Delivery of Murine Interleukin-2 (IL-2) and IL-6 by Recombinant Strains of Lactococcus lactis Coexpressing Antigen and Cytokine; Infection and Immunity, vol. 66, pp. 3183-3189, 1998.
Steidler et al., "Treatment of Murine Colitis by Lactococcus lactis Secreting Interleukin-10," Science, vol. 289, pp. 1352-1355, Aug. 25, 2000.
Frossard et al., "Oral administration of an IL-10-secreting Lactococcus lactis strain prevents food-induced IgE sensitization," Journal of Allergy and Clinical Immunology, vol. 119, No. 4, pp. 952-959, 2007.
Wells et al., "Improved cloning vectors and transformation procedure for Lactococcus lactis," Journal of Applied Bacteriology, vol. 74, No. 6, pp. 629-636, 1993.
Ahmed, Farid, "Genetically modified probiotics in foods," TRENDS in Biotechnology, vol. 21, No. 11, pp. 491-497, 2003.
Kleerebezem, et al., "Metabolic pathway engineering in lactic acid bacteria," Current Opinion in Biotechnology, vol. 14, No. 2, pp. 232-237, 2003.
De Valdez et al., "Protective Effect of Adonitol on Lactic Acid Bacteria Subjected to Freeze-Drying," Applied and Environmental Microbiology, vol. 45, No. 1, pp. 302-304, 1983.
Castro et al., "Evidence of membrane damage in Lactobacillus bulgaricus following freeze drying," Journal of Applied Microbiology, vol. 82, pp. 87-94, 1997.
Carvalho et al., "Protective effect of sorbitol and monosodium glutamate during storage of freeze-dried lactic acid bacteria," Le Lait, vol. 83, No. 3, pp. 203-210, 2003.
Huang et al., "Optimization of a protective medium for enhancing the viability of freeze-dried *Lactobacillus delbrueckii* subsp. *bulgaricus* based on response surface methodology," Journal of Independent Microbiology and Biotechnology, vol. 33, No. 1, pp. 55-61, 2006.
Huyghebaert et al., "Development of an enteric-coated formulation containing freeze-dried, viable recombinant Lactococcus lactis for the ileal mucosal delivery of human interleukin-10," European Journal of Pharmaceutics and Biopharmaceutics, vol. 60, pp. 349-359, 2005.
Berner et al., "Effect of protective agents on the viability of Lactococcus lactis subjected to freeze-thawing and freeze-drying," Scientia Pharmaceutica, vol. 74, pp. 137-149, 2006.
Carcoba et al., "Influence of cryptoprotectants on the viability and acidifying activity of frozen and freeze-dried calls of the novel starter strain *Lactococcus lactis* ssp. CECT 5180," European Food Research Technology, vol. 211, pp. 433-437, 2000.
Gibson et al., "Effects of Additives on the Survival of Lactic Streptococci in Frozen Storage," Applied Microbiology, vol. 14, No. 4, pp. 665-669, 1966.
Peebles et al., "Preparation of Concentrated Lactic Streptococcus Starters," Applied Microbiology, vol. 17, No. 6, pp. 805-810.
Hubalek, Zdenek, "Protectants used in the cryopreservation of microorganisms," Cryobiology, vol. 46, pp. 205-229, 2003.
Marie-Christine Chopin, Alain Chopin, Annette Rouault, and Nathalie Galleron, Insertion and Amplification of Foreign Genes in the *Lactococcus lactis* subsp. lactis Chromosome, 1989, Applied and Environmental Microbiology, vol. 55, No. 7, p. 1769-1774.

(56) References Cited

OTHER PUBLICATIONS

NPL document "CRITERION MRS broth" is a screenprint of webpage https://catalog.hardydiagnostics.com/cp_prod/Content!hugo/CRITN-LactobacilliM RSBroth. html accessed Jul. 11, 2016.

NPL pdf "Vegitone MRS Agar" obtained from Sigma-Aldrich website at http://www.sigmaaldrich.com/content!dam/sigmaaldrich/docs/Sigma-Aidrich/Datasheet/1/41782dat.pdf, accessed on Jul. 10, 2016, online since Jan. 21, 2006 according to Google.

NPL document "Media for Brewery, Winery and Fermentations" obtained from Sigma-Aldrich website at http://www.sigmaaldrich.com/analytical-chromatography/microbiology/microbiology-products.html?TablePage=17996750, accessed on Jul. 10, 2016, online since Oct. 27, 2008 according to Google.

NPL pdf "Dextrin from maize starch" is a screenprint of the webpage from Sigma-Aldrich at http://www.sigmaaldrich.com/catalog/search?te rm=9050-36-6&interface=CAS%20No.&N=0+&mode=partialmax&lang=en&region=US&focus=product, accessed 111/14/2015.

Samuel B. Leslie, Eitan Israel, Bruce Lighthart, John H. Crowe, and Lois M. Crowe, Trehalose and Sucrose Protect Both Membranes and Proteins in Intact Bacteria during Drying, 1995, Applied and Environmental Microbiology, vol. 61, No. 10, pp. 3592-3597.

Japanese Office Action dated Aug. 22, 2014 pertaining to Japanese Patent Application No. 507635/12 (Translation).

NPL pdf document "Guidance memorandum Mar. 4, 2014" accessed Mar. 27, 2014 from http://www.uspto.gov/patents/law/exam/myriad-mayo_guidance.pdf.

Klaenhammer et al., Discovering lactic acid bacteria by genomics, 2002, Lactic Acid Bacteria: Genetics, Metabolism and Applications, Proceedings of the seventh Symposium on lactic acid bacteria: genetics, metabolism and applications, Sep. 1-5, 2002, Egmond aan Zee, the Netherlands, Reprinted from Antonie van Leeuwenhoek, vol. 82, pp. 29-58.

R. Cárcoba & A. Rodriguez, Influence of cryoprotectants on the viability and acidifying activity of frozen and freeze-dried cells of the novel starter strain *Lactococcus lactis* ssp. lactis CECT 5180, 2000, Eur Food Res Technol, vol. 211, pp. 433-437.

R. I. N. Greaves, Preservation of Living Cells by Freeze-Drying, 1960, Annals of the Ney York Academy of Sciences, vol. 85, pp. 723-728.

X.C. Meng, C. Stanton, G. F. Fitzgerald, C. Daly, R.P. Ross, Anhydrobiotics: The challenges of drying probiotic cultures, 2008, Food Chemistry, vol. 106, pp. 1406-1416.

G. Zhao and G. Zhang, Effect of protective agents, freezing temperature, rehydration media on viability of malolactic bacteria subjected to freeze-drying, 2005, Journal of Applied Microbiology, vol. 99, pp. 333-338.

Office Action pertaining to Chinese Patent Application 201080018717.9 dated Aug. 14, 2012.

Zhiqiang et al., "Related Factors Influencing Freeze-dried Lactic Acid Bacteria Viability", Dairy Industry, pp. 51-53, Mar. 31, 2006 (article & English translation).

Search Report for PCT/EP2010/02604 dated Aug. 16, 2010.

Preliminary Report on Patentability for PCT/EP2010/002604 dated Nov. 10, 2011.

\* cited by examiner

SEQUENCE LISTING

```
<160> NUMBER OF SEQ ID NOS: 1

<210> SEQ ID NO 1
<211> LENGTH: 27
<212> TYPE: PRT
<213> ORGANISM: Lactococcus lactis
<220> FEATURE:
<221> NAME/KEY: MISC_FEATURE
<222> LOCATION: (1)..(27)
<223> OTHER INFORMATION: Secretion leader SSusp45

<400> SEQUENCE: 1

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala
            20                  25
```

CRYOPROTECTANTS FOR FREEZE DRYING OF LACTIC ACID BACTERIA

CROSS-REFERENCE TO RELATED APPLICATIONS

This application is a continuation of U.S. patent application Ser. No. 13/264,395, filed Oct. 14, 2011 (now U.S. Pat. No. 9,574,169, issued Feb. 21, 2017), which is the National Stage Entry of PCT/EP2010/002604, filed Apr. 28, 2010, which claims priority to EP09100265, filed Apr. 30, 2009, the contents of each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 13, 2020 is named 205350_0020_01_US_ST25.txt and is 794 bytes in size.

The present invention relates to the use of a novel combination of cryoprotectants for increasing the viability of lactic acid bacteria after freeze drying, improving the texture of the lyophilized cake for easy grinding and improving the long term stability of the freeze dried bacteria at different temperature conditions.

FIELD OF THE INVENTION

The invention is in the field of producing freeze dried bacteria, in particular Lactic acid bacteria. More in particular, the invention relates to the use of a novel combination of cryoprotectants for increasing the viability of bacteria after freeze drying, improving the texture of the lyophilized cake for easy grinding and improving the long term stability of the freeze dried bacteria at different temperature conditions. The invention further relates to such freeze dried bacteria for use in food industry or in human or animal health applications. More in particular, the invention relates to the increased viability and long-term storage of recombinant bacteria capable of expressing heterologous proteins or peptides and administered to humans or animals for therapeutic or vaccination purposes.

BACKGROUND OF THE INVENTION

Lactic acid bacteria (LAB) are a group of taxonomically diverse, Gram-positive bacteria that are able to convert fermentable carbohydrates mainly into lactic acid, acidifying the growth medium in the process. In general, LAB species are best known for their use in the food industry, mainly in the preparation of fermented foods such as dairy products and certain kinds of meat. The commercial significance of the dairy fermentation industry, which encompasses production of e.g. cheese, yoghurt and sour cream, is well recognized worldwide.

Over the past decades, interest in LAB has dramatically increased. The fact that selected LAB strains can influence the intestinal physiology is widely recognised. L. lactis has enjoyed a growing interest as production host for heterologous proteins, and eventually as in situ production and delivery system for biologically active molecules (see below).

At present, much effort has been directed towards the use of genetically engineered (GM) LAB species as production and delivery tools for topical, mucosal administration of biological drugs, including cytokines, antibody fragments, growth factors, hormones and neuropeptides. (e.g. [6-12]). In particular the engineered food-grade bacterium Lactococcus lactis (L. lactis) was chosen as the preferred microorganism for the therapeutic delivery of biologically active polypeptides. Clearly, the concept of oral therapeutic protein delivery by engineered L. lactis strains opens exciting possibilities. A necessary attribute of any pharmaceutical product however is long-term stability (shelf life), typically at least 24 months under predefined storage conditions. To this end, an efficient, scalable and reliable manufacturing platform needs to be developed for engineered L. lactis-based Drug Substance (DS) and Drug Product (DP) formulations.

During manufacturing and subsequent storage, the critical parameter for product stability is long-term viability of the engineered bacteria (normally expressed as colony forming units (CFU) per gram in function of storage time). Manufacture, storage and eventual therapeutic use of LAB strains imposes significant stress on the bacteria [4]. On industrial settings, LAB may be preserved and distributed in liquid, spray-dried, frozen or lyophilized (freeze-dried) forms. While all these preparations can be suitable for use as starter cultures in the food industry, emphasis is increasingly being placed on long-term preservation methods that promote high cell viability and metabolic activity, as these parameters are considered a prerequisite for (bio)pharmaceutical applications. In order to maximize survival, addition of selected cryoprotectants to the biomass and subsequent lyophilization are crucial steps, especially considering the fact that viable and metabolically active bacteria are an absolute requirement to induce the desired therapeutic effect in situ.

Freeze-drying is widely regarded as one of the most suitable dehydration processes for bacteria, aiming to achieve a solid and stable final formulation [4]. It is one of the most common methods to store microbial cell cultures, even though survival rates after freeze-drying and during storage may vary between strains [5]. Survival after freeze-drying reflects the ability of the cells to resist the effects of rapid freezing and drying, such as membrane lipid oxidation and cell damage at several target sites [5]. It is well known that the freeze-drying of unprotected bacteria kills most of them, and those that survive, die rapidly upon storage. Several attempts have therefore been made to increase the number of surviving bacteria upon lyophilization and storage, with limited success (see below).

Lyophilization is by far the most frequently, if not exclusively used method to achieve long-term shelf life [16]. The choice of an appropriate drying medium/cryoprotectant mixture is critical to increase the survival rate of LAB during lyophilization and subsequent storage [4]. Several studies attempting to increase the survival rate of LAB during freeze-drying and/or subsequent storage have been reported (for review, see [4]). However, none of these publications demonstrate sufficient long-term stability (i.e. >80% survival after one year) of the freeze-dried bacteria, as required for pharmaceutical applications, in particular at room temperature (25° C.) or at 2-8° C.

For most LAB cultures of commercial interest for the dairy industry, skim milk powder is selected as drying medium because it stabilizes the cell membrane constituents, facilitates rehydration and forms a protective coating over the cells [4]. Supplementing skim milk with additional cryoprotectants agents may enhance its intrinsic protective effect.

Font de Valdez et al. describe the protective effect of adonitol in 10% skim milk, on 12 strains of LAB subjected to freeze-drying [17]. Although high survival rates during lyophilization are reported (ranging from 42-100%, depending on the strain), no data on long-term stability were provided. Castro et al. assessed the beneficial effects of skim milk (11%) or trehalose (5%) on the survival of *Lactobacillus bulgaricus* after freeze-drying, showing retention rates of 25% (viable cell count) compared to ~1% in water alone [18]. Again, no data on stability during subsequent storage were reported.

Carvalho et al. (2003) demonstrated the stabilizing effect of either sorbitol or (mono)sodium glutamate (MSG), each added separately to LAB suspended in skim milk, on survival during lyophilization and subsequent storage for 3-6 months [19]. However, despite the fact that stability was increased compared to skim milk alone, the reported survival rates in the presence of sorbitol or MSG were still very low (<0.1%). Furthermore, long-term survival of the freeze-dried cells, stored in closed containers at 20° C. in air and kept in darkness for up to 8 months, showed a significant decrease of one or more logs over time.

Carcoba and Rodriguez studied the effects of various compounds, added individually to reconstituted skim milk (RSM), on cell survival and metabolic activity of *L. lactis* after freeze-drying [16]. They found that the sugars trehalose and sucrose, the polyols sorbitol and adonitol, as well as the amino acids β-alanine and glutamic acid, were capable of enhancing cell viability above the 44.3% recorded in RSM alone. However, actual survival rates with the supplemented media were not included, and no long-term storage data were disclosed.

As a final example, a study by Huang et al. developed and optimized a protective medium for *Lactobacillus delbrueckii*, resulting in a 86% cell viability after freeze-drying [20]. The composition of this medium was: sucrose 66.40 g/L, glycerol 101.20 g/L, sorbitol 113.00 g/L, and skim milk 130.00 g/L. Again, no long-term stability results were reported.

Huyghebaert et al. aimed to develop a freeze-dried powder formulation containing viable GM *L. lactis* bacteria with an acceptable shelf life [21]. To investigate the influence of the freeze-drying matrix, two different media were used; either M17 broth supplemented with 0.5% glucose (in order to obtain GM17), or 10% (w/v) skim milk supplemented with 0.5% glucose and 0.5% casein hydrolysate (in order to obtain GC-milk). Following freeze-drying, the influence of lyophilization parameters, freeze-drying matrix and different storage conditions was evaluated on short- and long-term viability.

When freeze-dried in conventional GM17 broth, absolute viability was less than 10%, while freeze-drying in GC-milk matrix resulted in significantly higher viability (60.0±18.0%). However, despite several attempts to standardize the freeze-drying procedure, significant batch-to-batch variability could not be avoided.

Short-term stability studies showed that viability already decreased ±20% after freeze-drying and storage for 1 week (GC-milk matrix). In long-term stability studies, relative viability was highly decreased after 1 month storage, followed by a logarithmic decrease during subsequent months of storage (GC-milk matrix, various storage conditions), indicating that long-term stability could not be achieved.

Considering the prior art in its entirety, it is obvious that skim milk is a recurrent component of freeze-drying media for LAB, and thus appears to be essential for bacterial viability. However, the use of milk derivatives in novel pharmaceutical compositions is strongly discouraged, especially in view of the Transmissible Spongiform Encephalopathy (TSE) risk associated with their use.

Next to high viability after production, freeze-dried LAB should also have an acceptable long-term shelf life for pharmaceutical applications. Stabilized dry bacterial compositions are for example described in US 2005/0100559, U.S. Pat. No. 3,897,307 and WO2004/065584. In US 2005/0100559 the dried bacterial composition are characterized in that they comprise a large fraction of stabilizers. See for example [055] in US 2005/0100559, wherein the stabilizers account for at least 40% (w/v). In WO2004/065584 sucrose or sucrose and maltodextrine were shown to improve the stability of a bacterial cell culture, but only at −20° C. In this reference there is no indication on how to improve the long-term shelf life (at room temperature) for a composition comprising freeze dried bacteria. In U.S. Pat. No. 3,897,307, all experiments start from a culture of different *Lactobacillus* species in nonfat milk that is subsequently freeze dried, optionally in the presence of stabilization potentiators selected from L-ascorbic acid, including edible salts thereof, and glutamic acid or aspartic acid, including the salts thereof. As such milk components are an important constituent of the stabilized dry bacterial compositions.

In other words none of the prior art addresses the replacement of the milk components with, sufficient survival and stability under long-term shelf storage. In fact, most of these studies lack precise data on initial viability, stability and bacterial density. Finally, none of them report on freeze-drying of GM bacteria and/or maintenance of their properties.

DETAILED DESCRIPTION OF THE INVENTION

Figure 1:
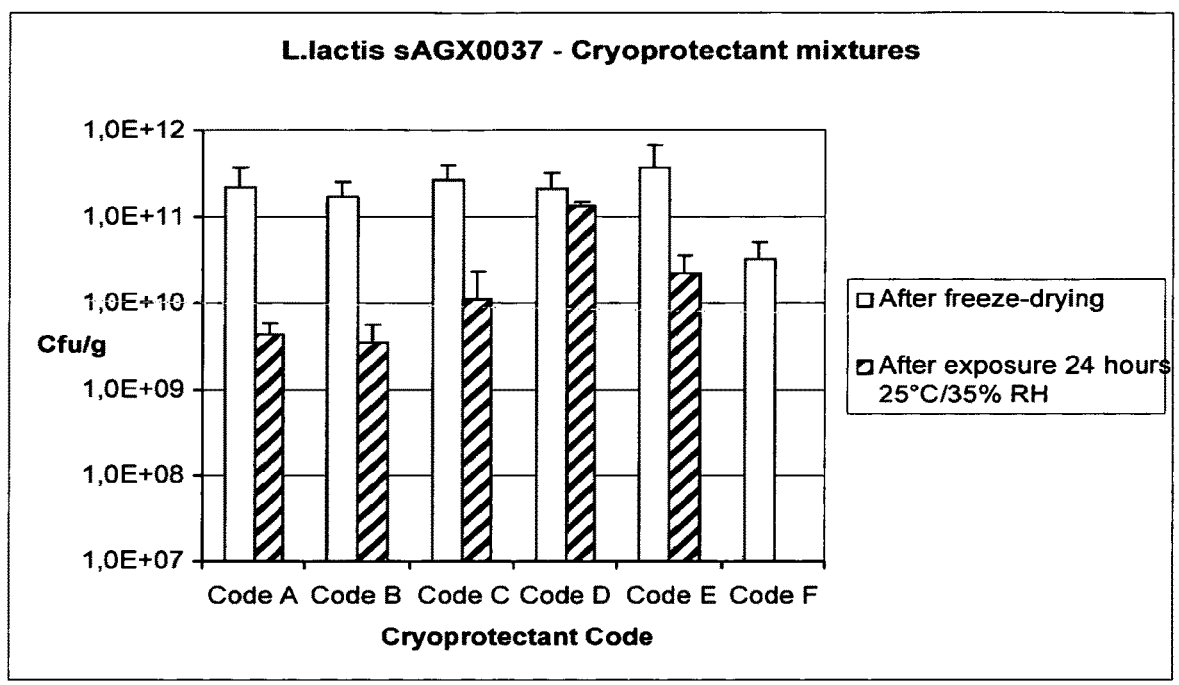
FIG. 1: Viable cell count (expressed in Colony Forming Units [CFU]/g) of *L. lactis* strain sAGX0037 using different cryoprotectant mixtures: data immediately after freeze-drying and after exposure to 25° C./35% RH for 24 hours. Detailed composition of the cryoprotectant mixtures is described in Table 1.

The present invention comprises the discovery and development of an effective cryoprotectant composition, without containing skim milk or any other animal-derived compounds, to achieve long-term stability of freeze-dried lactic acid bacteria (LAB), at different temperatures, whereby the retention of viability of the freeze-dried LAB after 6 months of storage, preferably after 9 months of storage, more preferably after 12 months of storage is more than 50%, preferably more than 60%, more preferably more than 70%, even more preferably more than 80%. The main advantage of the cryoprotectant composition formulation is to provide protection for the highly sensitive bacteria during freeze-drying, during short-term exposure to normal manufacturing operational conditions, and during long-term storage after packaging.

The present invention provides a combination of stabilizing agents (cryoprotectants), resulting in high survival of LAB upon freeze-drying, milling and sieving of the freeze-dried cakes and subsequent storage. In order to maximize survival, a combination of different stabilizing compounds (cryoprotectants) is added to the bacterial biomass before freeze-drying. This combination of stabilizing compounds, comprising a starch hydrolysate and a glutamic acid salt and/or a polyol, results in improved survival and stability of freeze-dried LAB. In particular, the invention relates to the use of a novel combination of cryoprotectants for increasing the viability of bacteria after freeze drying, improving the texture of the lyophilized cake for easy grinding and improving the long term stability of the freeze dried bacteria at different temperature conditions.

As explained in detail in the examples hereinafter, high viable cell yields (>6×10E+11 colony forming units [CFU]/g) were obtained after freeze-drying in the presence of the selected cryoprotectant mixture. Surprisingly, the viability of these freeze-dried cells was not affected by exposure to environmental conditions (mimicking downstream pharmaceutical formulation and production processes [e.g. capsule filling]) for 24 hours (25° C./35% RH), and long-term preservation of cell viability was observed at different storage conditions.

Cryoprotectant combinations containing either sodium glutamate or sorbitol and dextrane, combined with well-known cryoprotectants such as trehalose and sucrose, resulted in viable cell yields immediately after freeze-drying that were comparable to the preferred cryoprotectant formulation (code D). Short-term exposure studies clearly demonstrated that cryoprotectant formulations comprising such combination of a starch hydrolysate and a glutamic acid salt and/or a polyol, protect freeze-dried *L. lactis* bacteria upon unprotected storage for 24 hours at 25° C. and 35% RH. In the invention, the glutamic acid salt is preferably a sodium glutamate. The polyol of the invention is preferably sorbitol or mannitol, whereas the starch hydrolysate of the invention is preferably a dextran.

The results of the survival analysis for *Lactococcus lactis* (*L. lactis*) strain sAGX0037, determined by viable cell count on freeze-dried samples as well as samples exposed to air, indicated that a preferred combination (code D) of a starch hydrolysate (e.g. dextrane 500), sodium glutamate and a polyol (e.g. mannitol) (as presented in Examples 1, 2 and 3), protected the freeze-dried *L. lactis* bacteria upon unprotected storage for 24 hours at 25° C. and 35% RH.

Compared to a sucrose formulation, which is known as a "golden standard" for stabilisation of freeze-dried LAB, the combination of 3 cryoprotectants is clearly superior upon storage, and is the only combination of stabilisers that results in viable cell counts >6×10E+11 CFU/g upon short-term exposure to 25° C./35% RH. When sodium glutamate alone was added to the bacteria, upon short term exposure, no survival of the bacteria was observed.

The cryoprotectant combination of a starch hydrolysate (e.g. dextrin from maize starch), sodium glutamate and a polyol (e.g. sorbitol), leads to a stable freeze-dried LAB powder, assuring long-term stability and survival of viable bacteria (no significant decrease in viable cell count was observed on milled and sieved freeze-dried cakes stored at −20° C. and 5° C., and >90% of the initial viable cell count was preserved during 1 year of storage, resulting in very high CFU concentrations, up to >5×10E+11 CFU/g). At 25° C., 60% RH, only a slight decrease in viable cell count was observed, still resulting in high CFU concentrations, up to >3×10E+11 CFU/g after 1 year of storage at 25° C./60% RH.

It is accordingly an object of the present invention to provide a freeze dried bacterial composition comprising the combination of a starch hydrosylate, a glutamic acid salt and a polyl. As is evident from the examples hereinafter, the amount of starch hydrosylate as used in said composition is from about 2.0% to about 10% (w/v); in particular from about 2.5% to about 5% (w/v). The amount of glutamic acid salt as used in said composition is from about 2.0% to about 10% (w/v); in particular from about 5.0% to about 7.5% (w/v). The amount of polyol as used in said composition is from about 5.0% to about 30% (w/v); in particular from about 10% to about 20% (w/v); more in particular from about 7.5% to about 15% (w/v).

The 'polyols' as used herein, generally refers to a mixture of several sugar alcohols, such as sorbitol, maltitol, and mannitol, amongst others. It is hydrolyzed from corn starch, potato starch, or wheat starch, which is broken down into small units such as glucose, dextrin, malto-dextrin, and polydextrin, by amylase enzymes. In a subsequent hydrogenation step, said smaller units are converted into the sugar alcohols, such as sorbitol, maltitol, mannitol, and longer chain hydrogenated saccharides (such as maltitriitol). In a particular embodiment of the present invention the polyol is mannitol, sorbitol or a combination of sorbitol and mannitol. In said embodiment each of said polyol, i.e. sorbitol or mannitol, is each independently present in an amount from about 5.0% to about 15% (w/v); in particular from about 7.0% to about 15% (w/v). In an even further embodiment each of said polyol components are present in the same amount, i.e. at about 7%, 8%, 9%, 10%, 11%, 12%, 13%, 14% or 15% (w/v).

The 'glutamic acid salts' as used herein, generally refers to glutamic acid and its edible water-soluble salts. Such "edible" salts are those approved for use in human foods and are of food grade, such as the sodium and/or potassium salts of glutamic acid. In a particular embodiment of the present invention, the glutamic acid salt is monosodium glutamate, also known as sodium glutamate and MSG. In an even further embodiment said sodium glutamate is present from about 2.0% to about 10% (w/v); in particular from about 5.0% to about 7.5% (w/v).

The 'starch hydrosylates' as used herein generally refers to the hydrolization products of branched polysaccharides consisting of a large number of glucose units, such as starch, or dextran. In starch, the building units consist of the linear and helical amylose, and the branched amylopectin. In dextran, the straight chain consists of α-1,6 glycosidic linkages between glucose molecules, while branches begin from α-1,4 linkages (and in some cases, α-1,2 and α-1,3 linkages as well). In a particular embodiment the starch hydrosylates as used herein consist of any one of dextran, 1, dextran, 5, dextran 10, dextran 20, dextran, 40, dextran 60, dextran 70, dextran 110, or dextran 500. wherein the number refers to the normative molecular weight expressed in kDa; in a more particular embodiment the starch hydrosylate is dextran 500. In an even further embodiment said dextran is present from about 2.0% to about 10% (w/v); in particular from about 2.5% to about 5% (w/v).

As used in the description of the invention and examples, the singular forms "a", "an", and "the" include both singular and plural referents unless the context clearly dictates otherwise. By way of example, "a cell" refers to one or more than one cell.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within that range, as well as the recited endpoints.

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less from the specified value, insofar such variations are appropriate to perform in the disclosed invention.

All documents cited in the present specification are hereby incorporated by reference in their entirety. In particular, the teachings of all documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, ensuing definitions are included to better appreciate the teaching of the present invention.

The term "recombinant nucleic acid" refers generally to a nucleic acid which is comprised of segments joined together using recombinant DNA technology. When a recombinant nucleic replicates in a host organism, the progeny nucleic acids are also encompassed within the term "recombinant nucleic acid".

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980).

The term "heterologous", when referring to the relationship between a given ORF and a promoter, means that the said promoter is not normally associated with, i.e., is not normally controlling the transcription of, the said ORF in nature. In other words, the association is created by recombinant DNA techniques in the recombinant nucleic acids of the invention.

The term 'lactic acid bacterium' generally refers to a bacterium selected from the group consisting of a *Lactococcus* species, a *Lactobacillus* species, a *Streptococcus* species, a *Pediococcus* species, a *Bifidobacterium* species and a *Leuconostoc* species and encompasses any taxon (e.g., species, subspecies, strain) classified as belonging to such in the art.

The term "*Lactococcus*" generally refers to the genus *Lactococcus* and encompasses any taxon (e.g., species, subspecies, strain) classified as belonging to such in the art. By means of example, *Lactococcus* includes the species *Lactococcus garvieae, Lactococcus lactis, Lactococcus piscium, Lactococcus plantarum* and *Lactococcus raffinolactis*, and any subspecies and strains thereof.

In preferred embodiments of the invention the *Lactococcus* is *Lactococcus lactis*. *Lactococcus lactis* includes, without limitation, *Lactococcus lactis* ssp. *cremoris, Lactococcus lactis* ssp. *hordniae, Lactococcus lactis* ssp. *lactis, Lactococcus lactis* ssp. bv. *diacetylactis*.

In further preferred embodiments of the invention the *Lactococcus lactis* is *Lactococcus lactis* ssp. *cremoris* or *Lactococcus lactis* ssp. *lactis*, more preferably *Lactococcus lactis* ssp. *lactis*, and encompasses any strains thereof, such as, e.g., *Lactococcus lactis* ssp. *cremoris* SK11 or *Lactococcus lactis* ssp. *lactis* MG1363.

Accordingly, in an embodiment, the freeze-dried bacterium contains one or more open reading frames of the recombinant nucleic acids that encode an expression product, preferably a polypeptide, capable of eliciting a therapeutic response in a subject, preferably in a human or animal subject.

In a particularly useful, exemplary and not limiting, embodiment the said one or more open reading frames of the recombinant nucleic acids of the invention may encode an antigen and/or a non-vaccinogenic therapeutically active polypeptide.

As used herein, the term "antigen" generally refers to a substance foreign to a body (esp. to a body of a human or animal subject whereto the antigen is to be administered) that evokes an immune response, including humoral immunity and/or cellular immunity response, and that is capable of binding with a product, e.g., an antibody or a T cell, of the immune response. Hence, in a preferred example, an antigen requires a functioning immune system of a subject to which it is administered to elicit a physiological response from such a subject.

An antigen according to the invention may be derived from any polypeptide to which an immune response in a human or animal subject would be therapeutically useful, e.g., from a pathogen, e.g., from a viral, prokaryotic (e.g., bacterial) or eukaryotic pathogen, from a non-physiological protein (e.g., a protein derived from cancer tissue), from allergen (e.g., for eliciting immune tolerance), etc.

The term "a non-vaccinogenic therapeutically active polypeptide" refers generally to a polypeptide that, in a human or animal subject to which it is administered, does not elicit an immune response against itself and is able to achieve a therapeutic effect. Hence, the therapeutic effect of such a polypeptide would be expected to be directly linked to its own natural biological function whereby it can achieve particular effects in a body of a subject; rather than producing a therapeutic effect by acting as an immunogenic and/or immunoprotective antigen in the subject. Hence, the non-vaccinogenic therapeutically active polypeptide should be biologically active in its expressed form or, at least, must be converted into the biologically active form once released from the expressing host cell. Preferably, such biologically active form of the said polypeptide may display a secondary and preferably also tertiary conformation which is the same or closely analogous to its native configuration.

Preferably, the non-vaccinogenic therapeutically active polypeptide is also non-toxic and non-pathogenic.

In a preferred embodiment, the non-vaccinogenic therapeutically active polypeptide may be derived from human or animal, and may preferably correspond to the same taxon as the human or animal subject to which it is to be administered.

Non-limiting examples of suitable non-vaccinogenic therapeutically active polypeptides include ones which are capable of functioning locally or systemically, e.g., is a polypeptide capable of exerting endocrine activities affecting local or whole-body metabolism and/or the biologically active polypeptide(s) is/are one(s) which is/are capable of the regulation of the activities of cells belonging to the immunohaemopoeitic system and/or the one or more biologically active polypeptides is/are one(s) which is/are capable of affecting the viability, growth and differentiation of a variety of normal or neoplastic cells in the body or affecting the immune regulation or induction of acute phase inflammatory responses to injury and infection and/or the one or more biologically active polypeptides is/are one(s) which is/are capable of enhancing or inducing resistance to infection of cells and tissues mediated by chemokines acting on their target cell receptors, or the proliferation of epithelial cells or the promotion of wound healing and/or the one or more biologically active polypeptides modulates the expression or production of substances by cells in the body.

Specific examples of such polypeptides include, without limitation, insulin, growth hormone, prolactin, calcitonin, luteinising hormone, parathyroid hormone, somatostatin, thyroid stimulating hormone, vasoactive intestinal polypeptide, cytokines such as IL-2, IL-3, IL-4, IL-5, IL-6, IL-7, IL-9, IL-10, IL-11, IL-12, IL-13, any of IL-14 to IL-32, GM-CSF, M-CSF, SCF, IFNs, EPO, G-CSF, LIF, OSM, CNTF, GH, PRL, the TNF family of cytokines, e.g., TNFa, TNFb, CD40, CD27 or FAS ligands, the IL-1 family of cytokines, the fibroblast growth factor family, the platelet derived growth factors, transforming growth factors and nerve growth factors, the epidermal growth factor family of cytokines, the insulin related cytokines, etc. Alternatively, the therapeutically active polypeptide can be a receptor or antagonist for the therapeutically active polypeptides as defined above. Further specific examples of such suitable polypeptides are listed, e.g., in WO 96/11277, page 14, lines 1-30, incorporated herein by reference; in WO 97/14806, page 12, line 1 through page 13, line 27, incorporated herein by reference; or U.S. Pat. No. 5,559,007, col. 8, line 31 through col. 9, line 9, incorporated by reference herein.

Accordingly, in an embodiment the recombinant nucleic acid encodes an antigen and/or a non-vaccinogenic therapeutically active polypeptide, wherein the said antigen is capable of eliciting an immune response, preferably protective immune response, in a human or animal subject, and/or the said non-vaccinogenic therapeutically active polypeptide is capable of producing a therapeutic effect in a human or animal subject.

WO 97/14806 further specifically discloses co-expression of antigens with immune response stimulatory molecules, such as, e.g., interleukins, e.g., IL-2 or IL-6, by bacteria. Accordingly, freeze-dried bacteria of the invention for such co-expression are also contemplated.

In a further preferred embodiment, the open reading frame according to the invention further comprises a sequence encoding a secretion signal in phase with a polypeptide encoded by the ORF. This advantageously allows for secretion of the expressed polypeptide from the host cell and thereby may facilitate, e.g., isolation or delivery.

Typically, a secretion signal sequence represents an about 16 to about 35 amino acid segment, usually containing hydrophobic amino acids that become embedded in the lipid bilayer membrane, and thereby allow for the secretion of an accompanying protein or peptide sequence from the host cell, and which usually is cleaved from that protein or peptide. Preferably, the secretion signal sequence may be so-active in a host cell intended for use with the nucleic acid comprising the said signal sequence, e.g., a bacterial host cell, preferably a lactic acid bacterium, more preferably *Lactococcus*, even more preferably *Lactococcus lactis*.

Secretion signal sequences active in suitable host cells are known in the art; exemplary *Lactococcus* signal sequences include those of usp45 (see, U.S. Pat. No. 5,559,007) and others, see, e.g., Perez-Martinez et al. 1992 (Mol Gen Genet 234: 401-11); Sibakov et al. 1991 (Appl Environ Microbiol 57(2): 341-8). Preferably, the signal sequence is located between the promoter sequence and the ORF, i.e. the signal sequence is located 3' from the promoter sequence and precedes the ORF of the polypeptide of interest. In a preferred embodiment, the signal sequence encodes the amino acid sequence

```
                                      (SEQ ID NO: 1)
MKKKIISAIL MSTVILSAAA PLSGVYA (usp45).
```

In a further aspect, the freeze-dried bacterium of the invention comprises a vector containing a recombinant nucleic acid.

As used herein, "vector" refers to a nucleic acid molecule, typically DNA, to which nucleic acid fragments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, etc., as appropriate (see, e.g., Sambrook et al., 1989; Ausubel 1992).

The recombinant nucleic acid or the vector of the invention may be present in the host cell extra-chromosomally, preferably autonomously replicating using an own origin of replication, or may be integrated into bacterial genomic DNA, e.g., bacterial chromosome, e.g., *Lactococcus* chromosome. In the latter case, a single or multiple copies of the said nucleic acid may be integrated, preferably a single copy; the integration may occur at a random site of the chromosome or, as described above, at a predetermined site thereof, preferably at a predetermined site, such as, in a preferred non-limiting example, in the thyA locus of *Lactococcus*, e.g., *Lactococcus lactis*.

In a related aspect, the invention provides a method for the manufacturing of freeze-dried bacteria comprising one or more open reading frames within a recombinant nucleic acid within the freeze-dried bacteria to human or animal in need thereof, comprising administering to the said human or animal a therapeutically effective amount of such bacteria transformed with the said nucleic acid.

The animal may preferably be a mammal, such as, e.g., domestic animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on.

As used herein, the terms "treat" or "treatment" refer to both therapeutic treatment and prophylactic or preventative measures, wherein the object is to prevent or slow down (lessen) an undesired physiological change or disorder. A "human or animal in need of treatment" includes ones that would benefit from treatment of a given condition.

The term "therapeutically effective amount" refers to an amount of a therapeutic substance or composition effective to treat a disease or disorder in a subject, e.g., human or animal, i.e., to obtain a desired local or systemic effect and performance. By means of example, a therapeutically effective amount of bacteria may comprise at least 1 bacterium, or at least 10 bacteria, or at least $10^2$ bacteria, or at least $10^3$ bacteria, or at least $10^4$ bacteria, or at least $10^5$ bacteria, or at least $10^6$ bacteria, or at least $10^7$ bacteria, or at least $10^8$ bacteria, or at least $10^9$, or at least $10^{10}$, or at least $10^{11}$, or at least $10^{12}$, or at least $10^{13}$, or at least $10^{14}$, or at least $10^{15}$, or more host cells, e.g., bacteria, e.g., in a single or repeated dose.

The freeze-dried cells of the present invention may be administered alone or in combination with one or more active compounds. The latter can be administered before, after or simultaneously with the administration of the said freeze-dried cells.

A number of prior art disclosures on the delivery of antigens and/or therapeutically active polypeptides exist, and it shall be appreciated that such disclosures may be further advantageously modified with the strong promoters of the present invention. By means of example and not limitation, bacterial delivery of trefoil peptides may be used to treat diseases of the alimentary canal (see, e.g., WO 01/02570), delivery of interleukins in particular IL-10 for treating colitis (e.g., see WO 00/23471), delivery of antigens as vaccines (e.g., WO 97/14806), delivery of GLP-2 and related analogs may be used to treat short bowel disease, Crohn's disease, osteoporosis and as adjuvant therapy during cancer chemotherapy, etc. Further therapeutic applications are envisioned using the freeze-dried cells of the invention.

Further non-limiting examples of the types of diseases treatable in humans or animals by delivery of therapeutic polypeptides according to the invention include, but are not limited to, e.g., inflammatory bowel diseases including Crohn's disease and ulcerative colitis (treatable with, e.g., IL-Ira or IL-10 or trefoil peptides); autoimmune diseases, including but not limited to psoriasis, rheumatoid arthritis, lupus erythematosus (treatable with, e.g., IL-Ira or IL-10); neurological disorders including, but not limited to Alzheimer's disease, Parkinson's disease and amyotrophic lateral sclerosis (treatable with, e.g., brain devated neurotropic factor and ciliary neurotropic factor); cancer (treatable with, e.g., IL-1, colony stimulating factors or interferon-W); osteoporosis (treatable with, e.g., transforming growth factorf3); diabetes (treatable with, e.g., insulin); cardiovascular disease (treatable with, e.g., tissue plasminogen activator); atherosclerosis (treatable with, e.g., cytokines and cytokine antagonists); hemophilia (treatable with, e.g., clotting factors); degenerative liver disease (treatable with, e.g., hepatocyte growth factor or interferon a); pulmonary diseases such as cystic fibrosis (treatable with, e.g., alpha antitrypsin); obesity; pathogen infections, e.g., viral or bacterial infections (treatable with any number of the above-mentioned compositions or antigens); etc.

In a further aspect, the invention thus also provides a pharmaceutical composition comprising the freeze-dried bacteria manufactured by the invention, whether or not transformed with the nucleic acid and/or the vector described aboven.

Preferably, such formulation comprise a therapeutically effective amount of the freeze-dried bacteria manufactured by the invention and a pharmaceutically acceptable carrier, i.e., one or more pharmaceutically acceptable carrier substances and/or additives, e.g., buffers, carriers, excipients, stabilisers, etc. The term "pharmaceutically acceptable" as used herein is consistent with the art and means compatible with the other ingredients of a pharmaceutical composition and not deleterious to the recipient thereof. Freeze-dried bacteria lyophilized according to the invention may be prepared in the form of capsules, tablets, granulates and powders, each of which may be administered by the oral route.

Alternatively, freeze-dried bacteria lyophilized according to the invention may be prepared as aqueous suspensions in suitable media, or lyophilized bacteria may be suspended in a suitable medium just prior to use.

For oral administration, gastroresistant oral dosage forms may be formulated, which dosage forms may also include compounds providing controlled release of the host cells and thereby provide controlled release of the desired protein encoded therein. For example, the oral dosage form (including tablets, pellets, granulates, powders) may be coated with a thin layer of excipient (usually polymers, cellulosic derivatives and/or lipophilic materials) that resists dissolution or disruption in the stomach, but not in the intestine, thereby allowing transit through the stomach in favour of disintegration, dissolution and absorption in the intestine.

The oral dosage form may be designed to allow slow release of the host cells and of the recombinant protein thereof, for instance as controlled release, sustained release, prolonged release, sustained action tablets or capsules. These dosage forms usually contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery. When the compositions of the invention are to be administered rectally or vaginally, pharmaceutical formulations may include suppositories and creams. In this instance, the host cells are suspended in a mixture of common excipients also including lipids. Each of the aforementioned formulations are well known in the art and are described, for example, in the following references: Hansel et al. (1990, Pharmaceutical dosage forms and drug delivery systems, 5th edition, William and Wilkins); Chien 1992, Novel drug delivery system, 2nd edition, M. Dekker); Prescott et al. (1989, Novel drug delivery, J. Wiley & Sons); Cazzaniga et al., (1994, Oral delayed release system for colonic specific delivery, Int. J. Pharm.i08:7').

Preferably, an enema formulation may be used for rectal administration. The term "enema" is used to cover liquid preparations intended for rectal use. The enema may be usually supplied in single-dose containers and contains one or more active substances dissolved or dispersed in water, glycerol or macrogols or other suitable solvents.

Thus, according the invention, in a preferred embodiment, recombinant host cells encoding a desired gene may be administered to the animal or human via mucosal, e.g., an oral, nasal, rectal, vaginal or bronchial route by any one of the state-of-the art formulations applicable to the specific route. Dosages of host cells for administration will vary depending upon any number of factors including the type of bacteria and the gene encoded thereby, the type and severity of the disease to be treated and the route of administration to be used.

Thus, precise dosages cannot be defined for each and every embodiment of the invention, but will be readily apparent to those skilled in the art once armed with the present invention. The dosage could be anyhow determined on a case by case way by measuring the serum level concentrations of the recombinant protein after administration of predetermined numbers of cells, using well known methods, such as those known as ELISA or Biacore (See examples). The analysis of the kinetic profile and half life of the delivered recombinant protein provides sufficient information to allow the determination of an effective dosage range for the transformed host cells.

In an embodiment, when the freeze-dried bacteria manufactured in accordance with the inventions express an antigen, the invention may thus also provide a vaccine.

The term "vaccine" identifies a pharmaceutically acceptable composition that, when administered in an effective amount to an animal or human subject, is capable of inducing antibodies to an immunogen comprised in the vaccine and/or elicits protective immunity in the subject.

The vaccine of the invention would comprise the host cells transformed with the nucleic acids or vectors of the invention and further optionally an excipient. Such vaccines may also comprise an adjuvant, i.e., a compound or composition that enhances the immune response to an antigen. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful pharmaceutically acceptable human adjuvants such as BCG (bacille Calmetle-Guerin) and *Corynebacterium parvum*.

The freeze-dried lactic acid bacteria of the invention can be used in the food industry in general as a food additive or in particular as a starter culture, such as yoghurt starter cultures or cheese starter cultures. Typically, such compositions comprise the bacteria in a concentrated form including frozen, dried or freeze-dried concentrates typically having a concentration of viable cells which is at least $10^5$ CFU per gram of the composition, such as at least $10^6$ CFU/g including at least $10^7$ CFU/g, e.g. at least $10^8$ CFU/g, e.g. at least $10^{10}$ CFU/g, such as at least $10^{11}$ CFU/g, e.g. at least $10^{12}$ of the composition. The composition may as further components contain conventional additives including nutrients such as yeast extract, sugars and vitamins.

The invention provides for a method to manufacture freeze-dried lactic acid bacteria that are useful for a variety of edible product components or ingredients such as milk including non-pasteurized (raw) milk, meat, flour dough, wine and plant materials, such as vegetables, fruits or fodder crops. As used herein, the term "milk" is intended to mean any type of milk or milk component including e.g. cow's milk, human milk, buffalo milk, goat's milk, sheep's milk, dairy products made from such milk, or whey. The particular advantage of the freeze-dried lactic acid bacteria of the invention is the high level of viability and long-term storage capacity. The starter culture is added in amounts which result in a number of viable cells which is at least $10^3$ colony forming units (CFU) per gram of the edible product starting materials, such as at least $10^4$ CFU/g including at least $10^5$ CFU/g, such as at least $10^6$ CFU/g, e.g. at least $10^7$ CFU/g, such as at least $10^8$ CFU/g, e.g at least $10^9$ CFU/g, such as at least $10^{10}$ CFU/g, e.g. at least $10^{11}$ CFU/g, e.g. at least $10^{12}$/g of the edible product starting materials.

The invention also provides a freeze dried lactic acid bacterium comprising a combination of stabilizing compounds of the invention, which is in the form of a starter culture composition for the production of a food product or an animal feed, or in the form of a culture for the production of an aroma.

The invention is further illustrated with examples that are not to be considered limiting.

EXAMPLES

This invention will be better understood by reference to the Experimental Details that follow, but those skilled in the art will readily appreciate that these are only illustrative of the invention as described more fully in the claims that follow thereafter. Other embodiments will occur to the person skilled in the art in light of these examples, in particular embodiments comprising other lactic acid bacterium as *Lactococcus* species, such as a *Lactobacillus* species, a *Streptococcus* species, a *Pediococcus* species, a *Bifidobacterium* species and a *Leuconostoc* species and any to taxon (e.g., species, subspecies, strain) classified as belonging to such in the art.

Example 1: Stabilizing Effect of a Combination of Dextrane, Sodium Glutamate and a Polyol During Freeze-drying and Unprotected Short-term (24 Hours) Exposure to 25° C./35% RH

*L. Lactis* strain sAGX0037 was grown in a 5 L fermentor, washed twice with purified water that contained 800 μM thymidine, and concentrated tenfold. The concentrated bacteria were mixed in a 1:1 volume ratio with the cryoprotectant mixture (1 ml sample+1 ml cryoprotectant). The resulting formulation was aliquotted to 35 vials in 2 ml volumes. The entire process, from the bioreactor to the vial, took approximately 8 hours, while the temperature was averaging 10° C. The various formulations in their final concentration, i.e. including bacteria, are shown in Table 1. The vials were frozen in solid CO2 pellets until these were placed in the freeze-dryer.

TABLE 1

Composition of the cryoprotectant formulations after adding the cell suspension. The dry weight content of the cells in the formulated cell suspension was 33 g/L or 3.3%.

| Code | Final composition (weight/volume [w/v]) | Total solid cryoprotectant matter in final liquid formulation before freeze-drying (in % w/v) |
|---|---|---|
| A | 5% HES Hydroxy Ethyl Starch<br>5% trehalose<br>2.5% Sodium Glutamate | 12.5% |
| B | 4% sorbitol<br>4% dextrane 500<br>4% HES<br>4% trehalose<br>4% glycine | 20% |
| C | 7.5% HES<br>10% sucrose<br>2.5% Sodium Glutamate | 20% |
| D | 7.5% mannitol<br>7.5% Sodium Glutamate<br>3% glycine<br>2.5% dextrane 500 | 20.5% |
| E | 10% sucrose | 10% |
| F | no excipients added | |

In order to test the survival of the freeze-dried cakes after exposure to environmental conditions (mimicking downstream formulation processes [e.g. capsule filling]), 3 vials were analysed on viable cell count immediately after freeze-drying and after 24 hours of storage at 25° C. and 35% RH.

The results of the survival analysis for *L. lactis* strain sAGX0037, determined by viable cell count on the freeze-dried samples as well as the samples exposed to air, indicated that a combination of a starch hydrolysate (dextrane 500), sodium glutamate and a polyol (e.g. mannitol) (as presented by Code D), protected the freeze-dried *L. lactis* bacteria upon unprotected storage for 24 hours at 25° C. and 35% RH.

Although combinations containing either sodium glutamate or sorbitol and dextrane, combined with well-known cryoprotectants such as trehalose and sucrose (formulations coded A, B and C) resulted in viable cell yields immediately after freeze-drying that were comparable to the formulation coded D (>1×10E+11 CFU/g), short-term exposure studies clearly demonstrated that only formulation D, containing a combination of a starch hydrolysate and a glutamic acid salt and/or a polyol, protected freeze-dried *L. lactis* bacteria upon unprotected storage during 24 hours at 25° C. and 35% RH.

Compared to sucrose formulation (coded E), known as a "golden standard" for stabilisation of freeze-dried LAB, the selected combination (D) is superior upon storage, and is the only combination in this example resulting in a viable cell count >1×10E+11 CFU/g upon short-term exposure to 25° C./35% RH.

When no stabilisers were added to the bacteria, no survival of the bacteria was observed upon short-term exposure, as demonstrated in FIG. 1, formulation coded F.

Example 2: Stabilizing Effect of a Combination of Dextrane, Sodium Glutamate and a Polyol During Freeze-drying and Short-term (24 Hours) Exposure to 25° C./35% RH A pre-culture (100 ml) of *L. lactis* strain sAGX0037 was used for the inoculation of a 7 L Continuously Stirred Tank Reactor (CSTR), containing 5 L of M17c medium (composition listed in Table 2)

TABLE 2

Composition of M17c fermentation medium

| Component | Quantity (for 1 liter) |
|---|---|
| Yeast extract | 20 g |
| $KH_2PO_4$ | 2.0 g |
| $MgSO_4, 7H_2O$ | 0.51 g |
| Citric acid monohydrate | 0.49 g |
| Glucose | 55 g |
| Thymidine (100 mM) | 8 ml/L |

The bioreactor was set to maintain temperature at 30° C. and pH to 7 (by addition of 5M NH4OH). The agitation speed was set at 200 rpm. The fermentation was terminated when the glucose consumption was completed by cooling the fermentor to 4'C. An 'end of fermentation' sample was taken and used for dry cell weight (DCW) determination. Once the fermentation was terminated, 3.5 L of the fermentation broth was concentrated and washed by ultrafiltration/diafiltration using a 1400 cm2 500 kDa hollow fibre filter.

When the total amount of 3.5 L broth was concentrated approximately 10-fold, the 5 L bulk bottle was replaced with a bottle containing purified water and used for diafiltration. During diafiltration, the lactate concentration was monitored by analysis of the permeate. Diafiltration was terminated once the lactate concentration reached 5-10 g/L.

Directly after concentration and diafiltration, the bacterial cell suspensions were divided in 13 portions, to which different cryoprotectants were added (listed in Table 3). After mixing the cryoprotectants with the cell suspensions, each mixture was aliquotted over 25 vials (2 ml end volume) and freeze-dried.

TABLE 3

Composition of the cryoprotectant formulations after adding the cell suspension.
The dry weight content of the cells in the formulated cell suspension was 70 g/L

| Formulation code | Composition cryoprotectant Solution (w/v) | Total solid Cryoprotectant matter in final liquid formulation (% w/v) | Volume cell Suspension (ml) | Volume Cryoprotectant Solution (ml) |
|---|---|---|---|---|
| A1 | 10% HES<br>10% trehalose<br>5% Sodium Glutamate | 12.5% | 26 | 26 |
| A2 | 5% HES<br>10% trehalose<br>5% Sodium Glutamate | 10% | 26 | 26 |
| B1 | 8% sorbitol<br>8% dextrane 500<br>8% HES<br>8% trehalose<br>8% glycine | 20% | 26 | 26 |
| C1 | 15% HES<br>20% sucrose<br>5% Sodium Glutamate | 20% | 26 | 26 |
| C2 | 15% HES<br>15% sucrose<br>5% Sodium Glutamate | 12.5% | 26 | 26 |
| D1 | 15% mannitol<br>15% Sorbitol<br>5% Sodium Glutamate | 20.5% | 26 | 26 |

TABLE 3-continued

Composition of the cryoprotectant formulations after adding the cell suspension.
The dry weight content of the cells in the formulated cell suspension was 70 g/L

| Formulation code | Composition cryoprotectant Solution (w/v) | Total solid Cryoprotectant matter in final liquid formulation (% w/v) | Volume cell Suspension (ml) | Volume Cryoprotectant Solution (ml) |
|---|---|---|---|---|
| D2 | 6% glycine<br>5% dextrane 500<br>7% mannitol<br>7% Sorbitol<br>5% Sodium Glutamate<br>5% dextrane 500 | 12% | 26 | 26 |
| E1 | 50% sucrose | 10% | 41.6 | 10.4 |
| F2 | 40% sodium glutamate | 5% | 40 | 6.29 |

In order to test bacterial survival on the freeze-dried cakes after exposure to environmental conditions (mimicking downstream formulation processes [e.g. capsule filling]), 3 vials were analysed for viable cell count immediately after freeze-drying and after 24 hours of storage at 25° C. and 35% RH.

The results of the survival analysis for *L. lactis* strain sAGX0037, determined by viable cell count on the lyophilized samples as well as the samples exposed to air, indicated that a combination of a starch hydrolysate (dextrane 500), a polyol (e.g. mannitol and/or sorbitol) and sodium glutamate (as presented by code D1), yielded high viable cells count immediately after freeze-drying (e.g. >3 E+11 CFU/g) and stabilised the freeze-dried *L. lactis* bacteria upon unprotected storage for 24 hours at 25° C. and 35% RH, resulting in high viable cell yields (>2 E+11 CFU/g).

Although the formulations coded A1, A2, B1, C1 and C2 (combinations containing either sodium glutamate or sorbitol and dextrane, combined with well-known cryoprotectants such as trehalose and sucrose) resulted in viable cell yields immediately after freeze-drying that were comparable to the formulation coded D1, short-term exposure studies clearly demonstrated that formulations D1 and D2 (containing a mixture of at least a starch hydrolysate [dextrane 500], a polyol [e.g. mannitol and/or sorbitol] and sodium glutamate) stabilized the freeze-dried *L. lactis* bacteria upon unprotected storage during 24 hours at 25° C. and 35% RH.

Compared to sucrose formulation (coded E1), a "golden standard" for stabilisation of freeze-dried LAB, the combination of 3 cryoprotectants is clearly superior upon storage, and is the only combination of stabilisers in this example that resulted in a viable cell count >2×10E+11 CFU/g upon short-term exposure to 25° C./35% RH.

Figure 2:
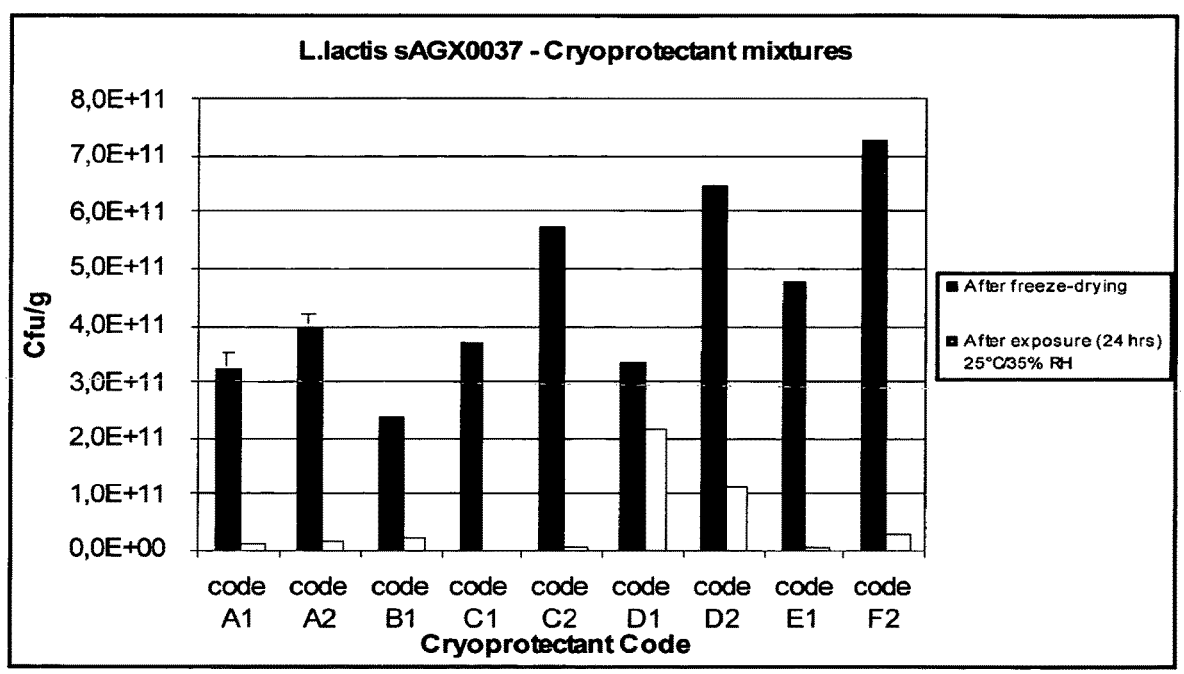
FIG. 2: Viable cell count (expressed in Colony Forming Units [CFU]/g) of *L. lactis* strain sAGX0037 using different cryoprotectant mixtures: data immediately after freeze-drying and after exposure to 25° C./35% RH for 24 hours. Detailed composition of the cryoprotectant mixtures is described in Table 3.

When sodium glutamate alone was added to the bacteria, no survival of the bacteria was observed upon short-term exposure, as demonstrated in FIG. 2, formulation coded F2.

Example 3: Stabilizing Effect of a Combination of Dextrane, Sodium Glutamate and Sorbitol During Freeze-drying and Unprotected Short-term (4 and 24 Hours) Exposure to 25° C./35% RH A pre-culture of *L. lactis* strain sAGX0037 (100 ml) was used for inoculation of a 7 L CSTR containing 5 L of M17c medium (see Table 2 above). The bioreactor was set to maintain temperature at 30° C. and pH to 7 (by addition of 5M NH4OH). The agitation speed was set to 200 rpm. The fermentation was terminated when the glucose concentration had dropped below 0.5 g/L, by cooling the fermentor to 4° C. An 'end of fermentation' sample was taken and used for DCW determination. Once the fermentation was terminated, 3.5 L of the fermentation broth was concentrated and washed by ultrafiltration/diafiltration using a 1400 cm2 500 kDa hollow fibre filter.

When the total amount of 3.5 L broth was concentrated approximately 10-fold, the 5 L bulk bottle was replaced with a bottle containing purified water, and used for diafiltration. During diafiltration, the lactate concentration was monitored by analysis of the permeate. Diafiltration was terminated once the lactate concentration reached 5-10 g/L.

The bacteria suspensions were mixed with different cryoprotectants, the composition of which is described in Table 4. After mixing the cryoprotectants with the suspensions, each mixture was aliquotted in different freeze-drying containers (55 ml aliquots) under aseptic conditions. After aliquotting, the containers were placed on a flat plate into a −70° C. freezer until freeze-drying. Two secondary drying temperatures were evaluated during the freeze-drying process: 25° C. and 35° C. shelf temperature.

TABLE 4

Composition of the cryoprotectant formulations after adding the cell suspension (dry weight of 70 g/L).

| Cryoprotectant code | Composition 5 × concentrated bulk solution (w/v) | Volume cell Suspension (ml) | Volume Cryoprotectant bulk solution (ml) | Final Cryoprotectant Mixture composition in liquid formulation before freeze-drying (% w/v) |
|---|---|---|---|---|
| Z4<br>25° C./35° C. | 20% Na-glutamate<br>10% dextrane 500<br>10% sorbitol | 184 | 46 | 4% Na-glutamate<br>2% dextrane 500<br>2% sorbitol |

Figure 3:
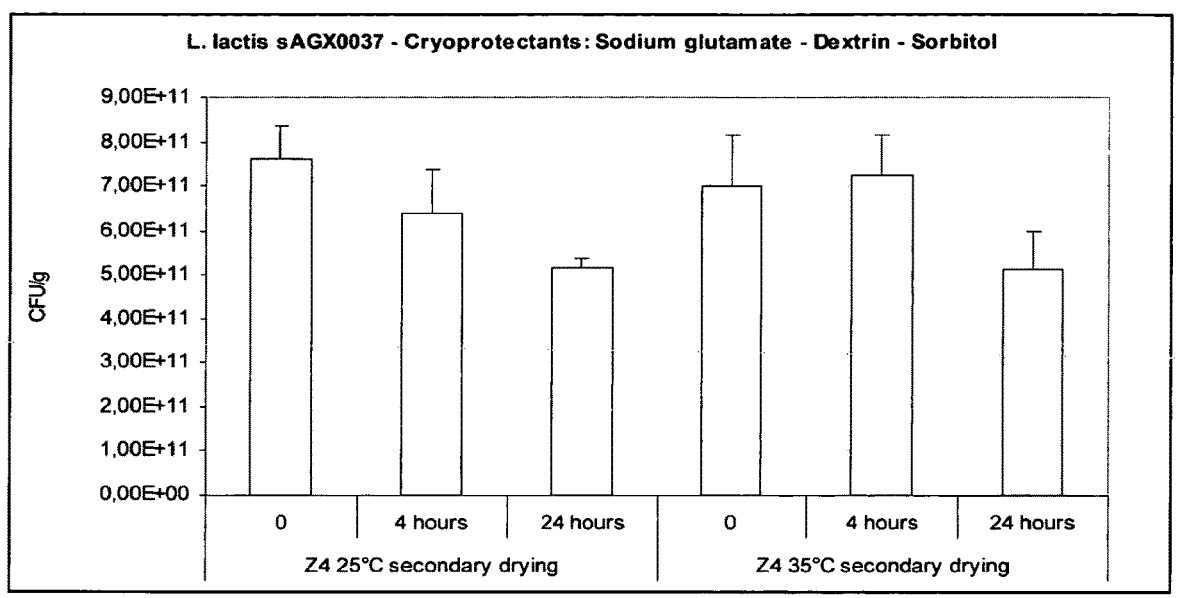
FIG. 3: Viable cell count (expressed in Colony Forming Units [CFU]/g) of *L. lactis* strain sAGX0037 using cryoprotectant mixture Z4 (20% sodium glutamate, 10% sorbitol and 10% dextrane 500), freeze-dried at final shelf temperature of 25° C. and 35° C.: data immediately after freeze-drying and after exposure to 25° C./35% RH for 4 and 24 hours. Detailed composition of the bacteria and cryoprotectants mixture composition is described in Table 4.

The results of the viability analysis for *L. lactis* strain sAGX0037 (FIG. 3), determined by viable cell count on the lyophilized samples as well as on the samples exposed to air, indicated that a combination of a starch hydrolysate (dextrane 500), a polyol (e.g. mannitol and/or sorbitol) and sodium glutamate, yielded high viable cell counts immediately after freeze-drying (e.g. >6 E+11 CFU/g) and stabilised the freeze-dried *L. lactis* bacteria upon unprotected exposure to 25° C. and 35% RH for 4 hours and 24 hours. High viable cell stability was observed after this exposure test, resulting in viable cell yields of >6 E+11 CFU/g after 4 hours and >5 E+11 CFU/g after 24 hours of exposure respectively.

TABLE 4A

Effect of cryoprotectant formulation on survival of *L. lactis* after freeze drying

| Sample | End composition Cryoprotectant mixture | Viable cell count CFU/ml before freeze drying | cell counting CFU/ml after freeze drying and reconstitution | Survival % |
|---|---|---|---|---|
| Z4 25° C. | 4% Na-glutamate 2% dextran 500 2% sorbitol | 1.6E+11 | 1.1E+11 | 69% |

Example 4: Stabilizing Effect of a Combination of Dextrin, Sodium Glutamate and Sorbitol During Freeze-drying and Long-Term Storage at Different Storage Conditions After a 200 L scale industrial fermentation of *L. lactis* strain sAGX0037, the accumulated biomass was concentrated and washed with purified water by ultrafiltration/diafiltration respectively. Diafiltration was stopped once the lactate concentration dropped below 5 g/L (55 mmol/L). During ultrafiltration and diafiltration, the vessel jacket was continuously water-cooled to 4° C.

In view of the subsequent lyophilization step, stabilization of the bacteria was ensured by addition of a selected cryoprotectant solution to the biomass resulting from the UF/DF step. The final cryoprotectant solution consisted of a starch hydrolysate (dextrin from maize starch), sodium glutamate and a polyol (sorbitol), as described in Table 5.

TABLE 5

Composition of the cryoprotectant formulation

| Component | Weight |
|---|---|
| Dextrin (from maize starch) | 100 g = 10% w/v |
| Sorbitol | 100 g = 10% w/v |
| Sodium glutamate | 200 g = 20% w/v |
| Water For Injections | QSP 1 L |

The required weight of the added cryoprotectant solution was approximately 17.0 kg cell suspension and 4.8 kg cryoprotectant solution, resulting in an approximate final formulation weight of 21.8 kg formulated cell suspension. The formulation was dispatched into suitable bulk lyophilization trays and freeze-dried under validated and monitored conditions. The trays were loaded onto the shelves of the freeze-dryer and subsequently frozen to −50° C. The total freezing time was approximately 9 hours.

After the freezing step, the chamber pressure was decreased and primary drying was started by increasing the shelf temperature in multiple ramp steps to −22° C., −10° C., 20° C., 25° C. and a final shelf temperature of 35° C. At the end of primary drying, a pressure rise test was performed to determine the end of the primary drying phase. No pressure rise occurred, and the freeze-drying process was continued by a secondary drying phase. The total time of the freeze-drying process was approximately 93 hours.

At the end of the freeze-drying cycle, the chamber was pressurized with dry, sterile-filtered nitrogen gas (filtered on a 0.22 µm pore size membrane). The trays were unloaded and packed into vapour-impermeable aluminium (Alu) foil pouches, at 18-26° C. and 30-70% RH respectively.

Then, the freeze-dried cakes were equilibrated for approximately one hour in a Class 100.000 production room at controlled temperature (19-23° C.) and humidity (<20% RH), and subsequently powdered by manual grinding (in PE bags) of the lyophilized cakes, followed by sieving (410 µm). After sieving, the powder was homogenized manually (in PE bags) and samples were taken from the resulting final freeze-dried bulk Drug Substance (DS, containing *L. lactis* sAGX0037 bacteria and cryoprotectants), for analysis and stability testing.

Figure 4:
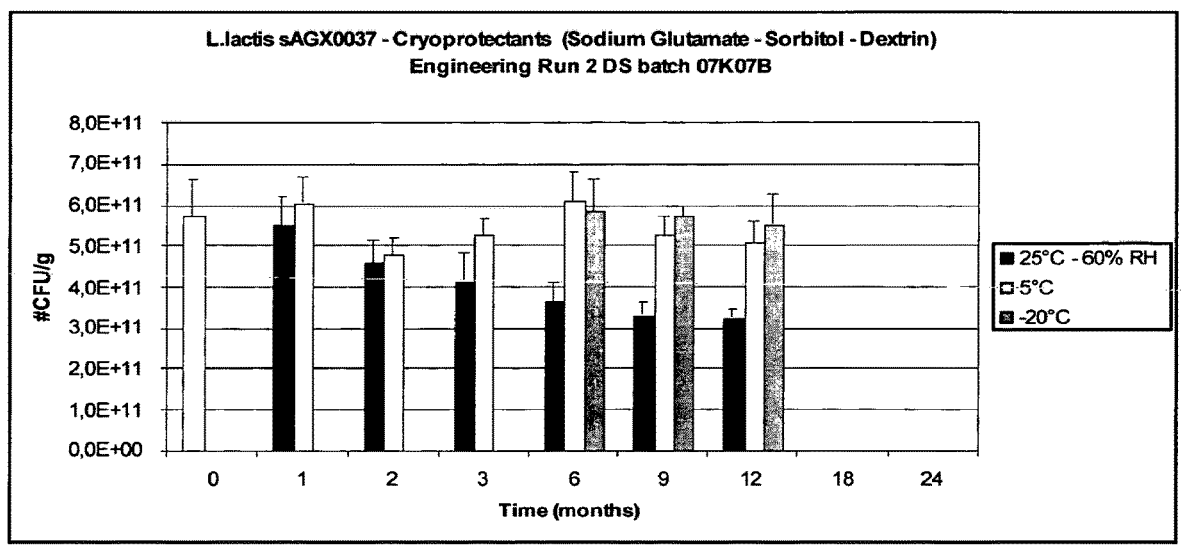
FIG. 4: Stabilizing effect of a combination of sodium glutamate, dextrin (from maize starch) and sorbitol on *L. lactis* strain sAGX0037 during freeze-drying and long-term storage at 3 different storage conditions: −20° C.; 5° C. and 25° C./60% RH in PET/ALU bags. Detailed composition of the bacteria and cryoprotectants mixture composition is described in Table 5.

Samples were packed per 500 mg in PET/Alu bags and stored at −20±5° C., at 5±3° C. and at 25±2° C., 60±5% RH. The samples were monitored during 12 months. As demonstrated in FIG. 4, no significant decrease in viable cell count was observed on the powdered, freeze-dried bacteria stored at −20° C. and 5° C., and >90% of the initial viable cell count was preserved during 1 year of storage, resulting in very high CFU concentrations of up to >5×10E+11 CFU/g. At 25° C., 60% RH, only a slight decrease in viable cell count was observed, resulting in high CFU concentrations of up to >3×10E+11 CFU/g after 1 year of storage at 25° C./60% RH.

These data clearly demonstrate that the cryoprotectant combination of a starch hydrolysate (e.g., dextrin from maize starch), sodium glutamate and a polyol (e.g. sorbitol) leads to a stable freeze-dried LAB powder, assuring long-term stability and survival of viable bacteria.

REFERENCES

1. Bibiloni R, Fedorak R N, Tannock G W, Madsen K L, Gionchetti P, Campieri M, De Simone C, Sartor R B. VSL#3 probiotic-mixture induces remission in patients with active ulcerative colitis. Am J Gastroenterol 2005; 100(7):1539-1546
2. Rioux K P, Fedorak R N. Probiotics in the treatment of inflammatory bowel disease. J Clin Gastroenterol 2006; 40(3):260-263
3. Shanahan F. Probiotics in inflammatory bowel disease—therapeutic rationale and role. Adv Drug Deliv Rev 2004; 56(6):809-818
4. Carvalho A S, Silva J, Ho P, Teixeira P, Malcata F X, Gibbs P. Relevant factors for the preparation of freeze-dried lactic acid bacteria. International Dairy Journal 2004; 14(10):835-847
5. Miyamoto-Shinohara Y, Sukenobe J, Imaizumi T, Nakahara T. Survival of freeze-dried bacteria. J Gen Appl Microbiol 2008; 54(1):9-24
6. Braat H, Rottiers P, Hommes D W, Huyghebaert N, Remaut E, Remon J P, van Deventer S J, Neirynck S, Peppelenbosch M P, Steidler L. A phase I trial with transgenic bacteria expressing Interleukin-10 in Crohn's disease. Clinical Gastroenterology and Hepatology 2006; 4:754-759
7. Vandenbroucke K, Hans W, Van Huysse J, Neirynck S, Demetter P, Remaut E, Rottiers P, Steidler L. Active delivery of trefoil factors by genetically modified *Lactococcus lactis* prevents and heals acute colitis in mice. Gastroenterology 2004; 127:502-513
8. Steidler L, Neirynck S, Huyghebaert N, Snoeck V, Vermeire A, Goddeeris B, Cox E, Remon J P, Remaut E. Biological containment of genetically modified *Lactococcus lactis* for intestinal delivery of human interleukin 10. Nat Biotechnol 2003; 21:785-789
9. Steidler L, Wells J M, Raeymaekers A, Vandekerckhove J, Fiers W, Remaut E. Secretion of biologically active murine interleukin-2 by *Lactococcus lactis* subsp. *lactis*. Applied and Environmental Microbiology 1995; 61:1627-1629
10. Steidler L, Robinson K, Chamberlain L, Schofield K M, Remaut E, Le Page R W F, Wells J M. Mucosal delivery of murine interleukin-2 (IL-2) and IL-6 by recombinant strains of *Lactococcus lactis* coexpressing antigen and cytokine. Infection and Immunity 1998; 66:3183-3189
11. Steidler L, Hans W, Schotte L, Neirynck S, Obermeier F, Falk W, Fiers W, Remaut E. Treatment of murine colitis by *Lactococcus lactis* secreting interleukin-10. Science 2000; 289:1352-1355
12. Frossard C P, Steidler L, Eigenmann P A. Oral administration of an IL-10-secreting *Lactococcus lactis* strain prevents food-induced IgE sensitization. J Allergy Clin Immunol 2007; 119(4):952-959
13. Wells J M, Wilson P W, Le Page R W. Improved cloning vectors and transformation procedure for *Lactococcus lactis*. J Appl Bacteriol 1993; 74(6):629-636
14. Ahmed F E. Genetically modified probiotics in foods. Trends Biotechnol 2003; 21(11):491-497
15. Kleerebezem M, Hugenholtz J. Metabolic pathway engineering in lactic acid bacteria. Curr Opi n Biotechnol 2003; 14(2):232-237
16. Carcoba R, Rodriguez A. Influence of cryoprotectants on the viability and acidifying activity of frozen and freeze-dried cells of the novel starter strain *Lactococcus lactis* ssp. *lactis* CECT 5180. European Food Research and Technology 2000; 211(6):433-437
17. de Valdez G F, de Giori G S, de Ruiz Holgado A A, Oliver G. Protective effect of adonitol on lactic acid bacteria subjected to freeze-drying. Appl Environ Microbiol 1983; 45(1):302-304
18. H. P. Castro P M T R K. Evidence of membrane damage in *Lactobacillus bulgaricus* following freeze drying. In; 1997:87-94
19. Ana S C, Joana S, Peter H, Paula T, Malcata F X, Paul G. Protective effect of sorbitol and monosodium glutamate during storage of freeze-dried lactic acid bacteria. In; 2003: 203-210
20. Huang L, Lu Z, Yuan Y, Lu F, Bie X. Optimization of a protective medium for enhancing the viability of freeze-dried *Lactobacillus delbrueckii* subsp. *bulgaricus* based on response surface methodology. J Ind Microbiol Biotechnol 2006; 33(1):55-61
21. Huyghebaert N, Vermeire A, Neirynck S, Steidler L, Remaut E, Remon J P. Development of an enteric-coated formulation containing freeze-dried, viable recombinant *Lactococcus lactis* for the ileal mucosal delivery of human interleukin-10. European Journal of Pharmaceutics and Biopharmaceutics 2005; 60:349-359

The invention claimed is:

1. A composition comprising:
   (a) a biomass of freeze dried *Lactococcus lactis* bacteria; and
   (b) stabilizing compounds, wherein a ratio of the biomass to the stabilizing compounds is no more than 1:1 (dry weight biomass to dry weight stabilizing compounds), wherein the stabilizing compounds consist of:
      (i) a starch hydrolysate, wherein the starch hydrolysate is selected from dextran and dextrin,
      (ii) a glutamic acid salt, and
      (iii) a polyol, wherein the polyol is selected from sorbitol and mannitol, and
   wherein the composition is free of milk.

2. The composition according to claim 1, wherein prior to freeze drying:
   the amount of starch hydrolysate ranges from about 2.0% to about 10% (w/v);
   the amount of glutamic acid salt ranges from about 2.0% to about 10% (w/v); and
   the amount of polyol ranges from about 5.0 to about 30% (w/v).

3. The composition according to claim 1, wherein the glutamic acid salt is sodium glutamate.

4. The composition according to claim 1, wherein the starch hydrolysate is dextran.

5. A method for freeze drying *Lactococcus lactis* bacteria comprising:
(a) providing a bacterial biomass comprising *Lactococcus lactis* bacteria;
(b) mixing the biomass with a combination of stabilizing compounds in a ratio of no more than 1:1 (dry weight biomass to dry weight stabilizing compounds) to form a composition, wherein the combination of stabilizing compounds consists of:
(1) a starch hydrolysate, wherein the starch hydrolysate is selected from dextran and dextrin,
(2) a glutamic acid salt, and
(3) a polyol, wherein the polyol is selected from sorbitol and mannitol; and
(c) freeze drying the composition,
wherein the composition is free of milk.

6. The composition according to claim 1, wherein the *Lactococcus lactis* bacterium comprises one or more recombinant nucleic acids which are heterologous to the *Lactococcus lactis* bacterium.

7. A culture or starter culture composition comprising the freeze dried composition according to claim 1.

8. A medicament comprising the freeze dried composition according to claim 1.

9. A food ingredient comprising the freeze dried composition according to claim 1.

10. A food product or animal feed comprising the culture or starter culture composition according to claim 7.

11. A composition comprising:
(a) a biomass of freeze dried *Lactococcus lactis* bacteria; and
(b) stabilizing compounds, wherein a ratio of the biomass to the stabilizing compounds is no more than 1:1 (dry weight biomass to dry weight stabilizing compounds), wherein the stabilizing compounds consist of:
(i) a starch hydrolysate selected from dextran and dextrin, wherein the amount of the starch hydrolysate ranges from about 5% to about 10% (w/v);
(ii) sodium glutamate, wherein the amount of the sodium glutamate ranges from about 5.0% to about 10% (w/v); and
(iii) a polyol selected from sorbitol and mannitol, wherein the amount of the polyol ranges from about 10% to about 20% (w/v), and
wherein the composition is free of milk.

12. The composition according to claim 11, wherein the starch hydrolysate is dextrin and the polyol is sorbitol.

13. The composition according to claim 11, wherein the freeze dried composition is free of animal-derived compounds.

14. The composition according to claim 1, wherein the *Lactococcus lactis* bacterium was cultured from a medium lacking milk.

15. The composition according to claim 1, wherein the composition is free of animal-derived compounds.

16. The composition according to claim 1, wherein the *Lactococcus lactis* bacterium in the composition retains at least 50% viability after 12 months when stored at −20° C. or 5° C.

17. The composition according to claim 1, wherein the *Lactococcus lactis* bacterium in the composition retains at least 80% viability after 12 months when stored at −20° C. or 5° C.

18. The composition according to claim 1, wherein the starch hydrolysate is dextrin and the polyol is sorbitol.

19. The composition according to claim 1, wherein the *Lactococcus lactis* bacterium is genetically modified.

\* \* \* \* \*